US009422265B2

(12) United States Patent
Li et al.

(10) Patent No.: US 9,422,265 B2
(45) Date of Patent: Aug. 23, 2016

(54) PROCESS FOR THE PREPARATION OF 3-(3-CHLORO-1H-PYRAZOL-1-YL)PYRIDINE

(71) Applicant: Dow AgroSciences LLC, Indianapolis, IN (US)

(72) Inventors: Xiaoyong Li, Midland, MI (US); Qiang Yang, Zionsville, IN (US); Beth Lorsbach, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/830,266

(22) Filed: Aug. 19, 2015

(65) Prior Publication Data

US 2016/0075681 A1    Mar. 17, 2016

Related U.S. Application Data

(60) Continuation of application No. 14/718,806, filed on May 21, 2015, now Pat. No. 9,156,813, which is a division of application No. 14/517,361, filed on Oct. 17, 2014, now Pat. No. 9,085,552.

(60) Provisional application No. 62/049,537, filed on Sep. 12, 2014.

(51) Int. Cl.
    *C07D 401/04* (2006.01)

(52) U.S. Cl.
    CPC ................... *C07D 401/04* (2013.01)

(58) Field of Classification Search
    CPC ..................................... C07D 401/04
    USPC ..................................... 546/275.4
    See application file for complete search history.

(56) References Cited

U.S. PATENT DOCUMENTS

| | | | |
|---|---|---|---|
| 3,597,341 A | 8/1971 | Oswald | |
| 4,080,457 A | 3/1978 | Harrison et al. | |
| 4,260,765 A | 4/1981 | Harrison et al. | |
| 4,407,803 A | 10/1983 | Haviv et al. | |
| 4,536,506 A | 8/1985 | Marcoux et al. | |
| 4,824,953 A | 4/1989 | Bronn | |
| 5,220,028 A | 6/1993 | Iwasawa et al. | |
| 5,625,074 A | 4/1997 | Daum et al. | |
| 5,631,380 A | 5/1997 | Haas et al. | |
| 5,652,372 A | 7/1997 | Muller et al. | |
| 5,693,657 A | 12/1997 | Lee et al. | |
| 5,750,718 A | 5/1998 | Muller et al. | |
| 5,817,677 A | 10/1998 | Linz et al. | |
| 5,854,264 A | 12/1998 | Anthony et al. | |
| 5,854,265 A | 12/1998 | Anthony et al. | |
| 5,869,681 A | 2/1999 | Muller et al. | |
| 6,040,331 A | 3/2000 | Yamamoto et al. | |
| 6,218,418 B1 | 4/2001 | Pevarello et al. | |
| 6,506,747 B1 | 1/2003 | Betageri et al. | |
| 6,548,525 B2 | 4/2003 | Galemmo, Jr. et al. | |
| 6,720,427 B2 | 4/2004 | Sanner et al. | |
| 6,878,196 B2 | 4/2005 | Harada et al. | |
| 6,916,927 B2 | 7/2005 | Bunnage et al. | |
| 6,965,032 B2 | 11/2005 | Freudenberger et al. | |
| 7,192,906 B2 | 3/2007 | Hirohara et al. | |
| 7,196,104 B2 | 3/2007 | Askew, Jr. et al. | |
| 7,319,108 B2 | 1/2008 | Schwink et al. | |
| 7,774,978 B2 | 8/2010 | Ding et al. | |
| 7,803,832 B2 | 9/2010 | Critcher et al. | |
| 7,910,606 B2 | 3/2011 | Nazare et al. | |
| 7,923,573 B2 | 4/2011 | Tamaki et al. | |
| 8,163,756 B2 | 4/2012 | Flynn et al. | |
| 8,222,280 B2 | 7/2012 | Liu et al. | |
| 8,901,153 B2 | 12/2014 | Buysse et al. | |
| 9,024,031 B1 | 5/2015 | Yang et al. | |
| 9,029,554 B1 | 5/2015 | Yang et al. | |
| 9,029,555 B1 | 5/2015 | Li et al. | |
| 9,029,556 B1 | 5/2015 | Yang et al. | |
| 9,044,017 B2 | 6/2015 | Yang et al. | |
| 9,085,552 B1 | 7/2015 | Li et al. | |
| 9,085,564 B2 | 7/2015 | Yang et al. | |
| 9,102,654 B2 | 8/2015 | Yang et al. | |
| 9,102,655 B2 | 8/2015 | Yang et al. | |
| 9,108,932 B2 | 8/2015 | Ross et al. | |
| 9,108,946 B2 | 8/2015 | Yang et al. | |
| 9,115,115 B1 | 8/2015 | Yang et al. | |
| 9,126,974 B2 | 9/2015 | Yang et al. | |
| 2002/0013326 A1 | 1/2002 | Tiebes et al. | |
| 2003/0153464 A1 | 8/2003 | Nakamura et al. | |
| 2003/0213405 A1 | 11/2003 | Harada et al. | |
| 2004/0043904 A1 | 3/2004 | Yamaguchi et al. | |

(Continued)

FOREIGN PATENT DOCUMENTS

| | | |
|---|---|---|
| EP | 0097323 | 1/1984 |
| EP | 0190457 | 8/1986 |

(Continued)

OTHER PUBLICATIONS

Kempe et al., "Responsive Glyco-poly(2-oxaoline)s: Synthesis, Cloud Point Tuning, and Lectin Binding," Biomacromolecules 2011, vol. 12, pp. 2591-2600.
Fields et al., "Preparation of Trifluoromethyl-Pyrazoles and -Pyrazolines by the Reaction of 2,2,2-Trifluorodiazoethane with Carbon-Carbon Multiple Bonds," Journal of Fluorine Chemistry, 1979, vol. 13, pp. 147-158.
Bradbury et al., "Enzyme-catalysed peptide amidation," Eur. J. Biochem. 1987, vol. 169, pp. 579-584.
International Search Report and Written Opinion for PCT/US2014/061005 mailed Dec. 16, 2014.
International Search Report and Written Opinion for PCT/US2014/061006 mailed Dec. 8, 2014.

(Continued)

*Primary Examiner* — Patricia L Morris
(74) *Attorney, Agent, or Firm* — Carl D. Corvin; Barnes & Thornburg LLP

(57) ABSTRACT

This disclosure relates to the field of preparation of 3-(3-chloro-1H-pyrazol-1-yl)pyridine and intermediates therefrom. These intermediates are useful in the preparation of certain pesticides.

7 Claims, No Drawings

(56) References Cited

U.S. PATENT DOCUMENTS

| | | |
|---|---|---|
| 2004/0082629 A1 | 4/2004 | Iwataki et al. |
| 2005/0038059 A1 | 2/2005 | Mueller et al. |
| 2005/0176710 A1 | 8/2005 | Schwink et al. |
| 2006/0135778 A1 | 6/2006 | Schnatterer et al. |
| 2006/0160857 A1 | 7/2006 | Buettelmann et al. |
| 2006/0160875 A1 | 7/2006 | Gaines et al. |
| 2006/0167020 A1 | 7/2006 | Dickerson et al. |
| 2006/0287365 A1 | 12/2006 | Billen et al. |
| 2006/0287541 A1 | 12/2006 | Nishino et al. |
| 2007/0049604 A1 | 3/2007 | Nam et al. |
| 2007/0167426 A1 | 7/2007 | Siddiqui et al. |
| 2008/0004301 A1 | 1/2008 | Tamaki et al. |
| 2008/0027046 A1 | 1/2008 | Annan et al. |
| 2009/0023709 A1 | 1/2009 | Gillespie et al. |
| 2009/0069288 A1 | 3/2009 | Breinlinger et al. |
| 2009/0137524 A1 | 5/2009 | Billen et al. |
| 2009/0325956 A1 | 12/2009 | Taniguchi et al. |
| 2010/0130474 A1 | 5/2010 | Bothmann et al. |
| 2010/0204164 A1 | 8/2010 | Crouse et al. |
| 2010/0286169 A1 | 11/2010 | Guiles et al. |
| 2010/0292253 A1 | 11/2010 | Trullinger et al. |
| 2010/0305200 A1 | 12/2010 | Velicelebi et al. |
| 2011/0021771 A1 | 1/2011 | Mallais et al. |
| 2011/0048261 A1 | 3/2011 | Shimura |
| 2011/0098287 A1 | 4/2011 | Bretschneider et al. |
| 2011/0118290 A1 | 5/2011 | Bretschneider et al. |
| 2011/0166129 A1 | 7/2011 | Machacek et al. |
| 2011/0166143 A1 | 7/2011 | Bretschneider et al. |
| 2011/0184188 A1 | 7/2011 | Wada et al. |
| 2011/0201649 A1 | 8/2011 | Matsuzaki et al. |
| 2011/0212949 A1 | 9/2011 | Bretschneider et al. |
| 2011/0275583 A1 | 11/2011 | Bretschneider et al. |
| 2011/0319428 A1 | 12/2011 | Fublein et al. |
| 2012/0053146 A1 | 3/2012 | Parker et al. |
| 2012/0094837 A1 | 4/2012 | Muhlthau et al. |
| 2012/0095023 A1 | 4/2012 | Bretschneider et al. |
| 2012/0101294 A1 | 4/2012 | Hirota et al. |
| 2012/0110701 A1 | 5/2012 | Garizi et al. |
| 2012/0110702 A1 | 5/2012 | Yap et al. |
| 2012/0115811 A1 | 5/2012 | Du et al. |
| 2012/0165345 A1 | 6/2012 | Bretschneider et al. |
| 2012/0172218 A1 | 7/2012 | Crouse et al. |
| 2012/0220453 A1 | 8/2012 | Lowe et al. |
| 2012/0252770 A1 | 10/2012 | Berger et al. |
| 2013/0072382 A1 | 3/2013 | Trullinger et al. |
| 2013/0089622 A1 | 4/2013 | Trullinger et al. |
| 2013/0109566 A1 | 5/2013 | Niyaz et al. |
| 2013/0261141 A1 | 10/2013 | Bretschneider et al. |
| 2013/0288893 A1 | 10/2013 | Buysse et al. |
| 2013/0291227 A1 | 10/2013 | Buysse et al. |
| 2013/0324736 A1 | 12/2013 | Ross, Jr. et al. |
| 2013/0324737 A1 | 12/2013 | Ross, Jr. et al. |
| 2013/0338367 A1 | 12/2013 | Numata et al. |
| 2014/0162874 A1 | 6/2014 | Yap et al. |

FOREIGN PATENT DOCUMENTS

| | | |
|---|---|---|
| EP | 0205024 | 12/1986 |
| EP | 0248315 | 12/1987 |
| EP | 0425948 | 5/1991 |
| EP | 1273582 | 1/2003 |
| EP | 1321463 | 6/2003 |
| EP | 1329160 | 7/2003 |
| JP | 1987-153273 | 7/1987 |
| JP | 1988-174905 | 7/1988 |
| JP | 1989-226815 | 9/1989 |
| JP | 2003-212864 | 7/2003 |
| JP | 2004-051628 | 2/2004 |
| JP | 2004-292703 | 10/2004 |
| JP | 2012-188418 | 10/2012 |
| JP | 2013-075871 | 4/2013 |
| JP | 2013-082699 | 5/2013 |
| JP | 2013-082704 | 5/2013 |
| JP | 2013-107867 | 6/2013 |
| JP | 2013-129651 | 7/2013 |
| JP | 2013-129653 | 7/2013 |
| WO | 94/13644 | 6/1994 |
| WO | 97/36897 | 10/1997 |
| WO | 98/49166 | 11/1998 |
| WO | 00/35919 | 6/2000 |
| WO | 01/34127 | 5/2001 |
| WO | 01/90078 | 11/2001 |
| WO | 02/083111 | 10/2002 |
| WO | 03/008405 | 1/2003 |
| WO | 03/072102 | 9/2003 |
| WO | 2004/041813 | 5/2004 |
| WO | 2005/070925 | 8/2005 |
| WO | 2005/074875 | 8/2005 |
| WO | 2006/023462 | 3/2006 |
| WO | 2006/033005 | 3/2006 |
| WO | 2006/046593 | 5/2006 |
| WO | 2006/103045 | 10/2006 |
| WO | 2007/005838 | 1/2007 |
| WO | 2007/087427 | 8/2007 |
| WO | 2007/098826 | 9/2007 |
| WO | 2008/005457 | 1/2008 |
| WO | 2008//079277 | 7/2008 |
| WO | 2008/090382 | 7/2008 |
| WO | 2011/045224 | 10/2009 |
| WO | 2009/149858 | 12/2009 |
| WO | 2010/006713 | 1/2010 |
| WO | 2010/009290 | 1/2010 |
| WO | 2010/012442 | 2/2010 |
| WO | 2010/033360 | 3/2010 |
| WO | 2010/035011 | 4/2010 |
| WO | 2010/048207 | 4/2010 |
| WO | 2010/060379 | 6/2010 |
| WO | 2010/075376 | 7/2010 |
| WO | 2010/129497 | 11/2010 |
| WO | 2010/133336 | 11/2010 |
| WO | 2010/146236 | 12/2010 |
| WO | 2011/003065 | 1/2011 |
| WO | 2011/043371 | 4/2011 |
| WO | 2011/045240 | 4/2011 |
| WO | 2011/091153 | 7/2011 |
| WO | 2011/101229 | 8/2011 |
| WO | 2011/126903 | 10/2011 |
| WO | 2011/128304 | 10/2011 |
| WO | 2011-134964 | 11/2011 |
| WO | 2011/138285 | 11/2011 |
| WO | 2011/163518 | 12/2011 |
| WO | 2012/000896 | 1/2012 |
| WO | 2012/004217 | 1/2012 |
| WO | 2012/007500 | 1/2012 |
| WO | 2012/052412 | 4/2012 |
| WO | 2012/061290 | 5/2012 |
| WO | 2012/070114 | 5/2012 |
| WO | 2012/102387 | 8/2012 |
| WO | 2012/108511 | 8/2012 |
| WO | 2012/147107 | 11/2012 |
| WO | 2012/168361 | 12/2012 |
| WO | 2013/000931 | 1/2013 |
| WO | 2013/010946 | 1/2013 |
| WO | 2013/010947 | 1/2013 |
| WO | 2013/062980 | 5/2013 |
| WO | 2013/062981 | 5/2013 |
| WO | 2013/064324 | 5/2013 |
| WO | 2013/156431 | 10/2013 |
| WO | 2013/156433 | 10/2013 |

OTHER PUBLICATIONS

International Search Report and Written Opinion for PCT/US2014/061007 mailed Dec. 31, 2014.
International Search Report and Written Opinion for PCT/US2014/061009 mailed Dec. 8, 2014.
International Search Report and Written Opinion for PCT/US2014/061010 mailed Dec. 15, 2014.
International Search Report and Written Opinion for PCT/US2014/061012 mailed Dec. 15, 2014.
International Search Report and Written Opinion for PCT/US2014/061014 mailed Dec. 15, 2014.
International Search Report and Written Opinion for PCT/US2014/061016 mailed Dec. 15, 2014.

(56) References Cited

OTHER PUBLICATIONS

International Search Report and Written Opinion for PCT/US2014/061022 mailed Dec. 29, 2014.
International Search Report and Written Opinion for PCT/US2014/061023 mailed Dec. 15, 2014.
International Search Report and Written Opinion for PCT/US2014/061024 mailed Dec. 15, 2014.
International Search Report and Written Opinion for PCT/US2014/061027 mailed Dec. 15, 2014.
International Search Report and Written Opinion for PCT/US2014/061029 mailed Dec. 15, 2014.
International Search Report and Written Opinion for PCT/US2014/061030 mailed Dec. 15, 2014.
International Search Report and Written Opinion for PCT/US2013/029615 mailed May 8, 2013.
Ameduri, B. et al., "Synthesis and polymerization of fluorinated monomers bearing a reactive lateral group Part 4. Preparation of functional perfluorovinyl monomers by radical addition of functional mercaptans to 1,1,2-trifluoro-1,4-pentadiene." J. Fluorine Chemistry, 92, 77-84 (1998).
International Preliminary Report on Patentability for PCT/US2011/058578 mailed Dec. 21, 2012.
International Search Report and Written Opinion for PCT/US2011/058578 mailed Apr. 5, 2012.

PROCESS FOR THE PREPARATION OF 3-(3-CHLORO-1H-PYRAZOL-1-YL)PYRIDINE

CROSS REFERENCE TO RELATED APPLICATIONS

This Application is a continuation of U.S. application Ser. No. 14/718,806 filed on May 21, 2015, which is a divisional of U.S. application Ser. No. 14/517,361 filed on Oct. 17, 2014, which claims the benefit of U.S. Provisional Patent Application Ser. No. 62/049,537, filed Sep. 12, 2014, the entire disclosures of which are hereby expressly incorporated by reference into this Application.

TECHNICAL FIELD

This disclosure relates to the field of preparation of 3-(3-chloro-1H-pyrazol-1-yl)pyridine and intermediates therefrom. These intermediates are useful in the preparation of certain pesticides.

BACKGROUND

US 20130288893(A1) describes certain (3-halo-1-(pyridin-3-yl)-1H-pyrazol-4-yl)amides and carbamates and their use as pesticides. The processes therein to prepare these amides and carbamates result in low yields, rely on a starting material that is difficult to prepare (3-chloropyrazole), and provide a product that is difficult to isolate in a pure form. It would be desirable to have a process for preparing 3-(3-chloro-1H-pyrazol-1-yl)pyridine that avoids these problems.

DETAILED DESCRIPTION

The following definitions apply to the terms as used throughout this specification, unless otherwise limited in specific instances.

As used herein, the term "alkyl" denotes branched or unbranched hydrocarbon chains.

As used herein, the term "alkoxide" means an alkyl further consisting of a carbon-oxygen single bond, for example, methoxy, ethoxy, propoxy, isopropoxy, butoxy, isobutoxy, and tert-butoxy.

The present disclosure provides an alternative process for preparing 3-(3-chloro-1H-pyrazol-1-yl)pyridine (5b) by cyclizing 3-hydrazinopyridine•dihydrochloride with an alkyl methacrylate to provide 4-methyl-1-(pyridin-3-yl)pyrazolidin-3-one (1), by chlorinating (1) to provide 3-(3-chloro-4-methyl-4,5-dihydro-1H-pyrazol-1-yl)pyridine (2), by oxidizing (2) to provide 3-(3-chloro-4-methyl-1H-pyrazol-1-yl)pyridine (3), by further oxidizing (3) to provide 3-chloro-1-(pyridin-3-yl)-1H-pyrazole-4-carboxylic acid (4), and by decarboxylating (4) to provide 3-(3-chloro-1H-pyrazol-1-yl)pyridine (5b).

Thus, the present disclosure concerns a process for preparing 3-(3-chloro-1H-pyrazol-1-yl)pyridine (5b)

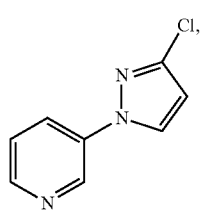

(5b)

which comprises a) cyclizing 3-hydrazinopyridine•dihydrochloride

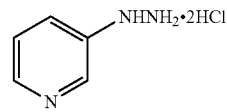

with alkyl methacrylate,

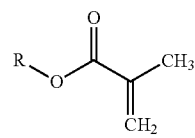

wherein R represents ($C_1$-$C_4$) alkyl, in a ($C_1$-$C_4$) alkyl alcohol at a temperature of about 25° C. to about 80° C. in the presence of an alkali metal ($C_1$-$C_4$) alkoxide to provide 4-methyl-1-(pyridin-3-yl)pyrazolidin-3-one (1)

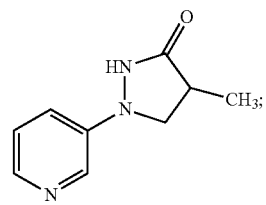

(1)

b) chlorinating 4-methyl-1-(pyridin-3-yl)pyrazolidin-3-one (1) with a chlorinating reagent in an organic solvent at a temperature of about 25° C. to about 100° C. to provide 3-(3-chloro-4-methyl-4,5-dihydro-1H-pyrazol-1-yl)pyridine (2)

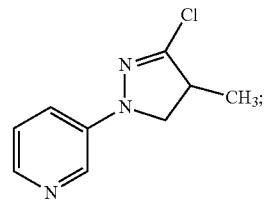

(2)

c) oxidizing 3-(3-chloro-4-methyl-4,5-dihydro-1H-pyrazol-1-yl)pyridine (2) with an oxidant in a solvent at a temperature of about 25° C. to about 100° C. to provide 3-(3-chloro-4-methyl-1H-pyrazol-1-yl)pyridine (3)

(3)

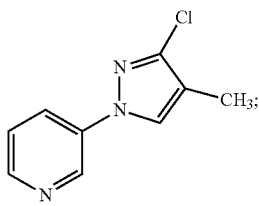

d) further oxidizing 3-(3-chloro-4-methyl-1H-pyrazol-1-yl)pyridine (3) with an oxidant in a polar protic solvent at a temperature of about 50° C. to about 100° C. to provide 3-chloro-1-(pyridin-3-yl)-1H-pyrazole-4-carboxylic acid (4)

(4)

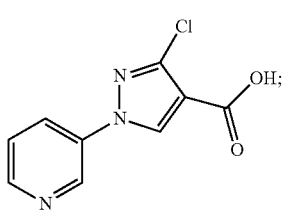

and e) decarboxylating 3-chloro-1-(pyridin-3-yl)-1H-pyrazole-4-carboxylic acid (4) with copper oxide in a polar aprotic solvent at a temperature of about 80° C. to about 180° C. to provide 3-(3-chloro-1H-pyrazol-1-yl)pyridine (5b).

Scheme 1 outlines this process for preparing 3-(3-chloro-1H-pyrazol-1-yl)pyridine (5b).

Scheme 1

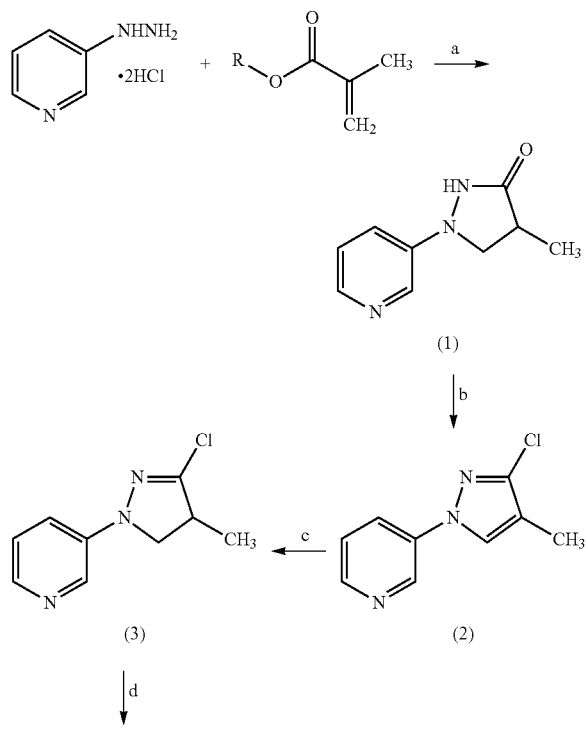

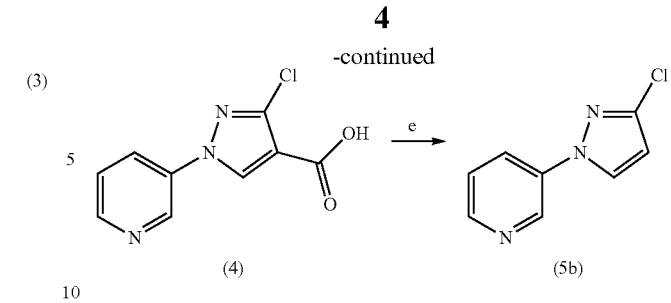

In step 1a, 3-hydrazinopyridine·dihydrochloride is cyclized with a ($C_1$-$C_4$) alkyl methacrylate, in a solution further comprising a ($C_1$-$C_4$) alkyl alcohol and an alkali metal ($C_1$-$C_4$) alkoxide, to provide 4-methyl-1-(pyridin-3-yl)pyrazolidin-3-one (1). Step a is conducted at a temperature from about 25° C. to about 80° C. While stoichiometric amounts of 3-hydrazinopyridine·dihydrochloride and ($C_1$-$C_4$) alkyl methacrylate may be used, it is often convenient to use about a 1.5 fold to about a 2 fold excess of ($C_1$-$C_4$) alkyl methacrylate compared to 3-hydrazinopyridine·dihydrochloride. The ($C_1$-$C_4$) alkyl alcohol is preferably selected from methanol, ethanol, propanol, butanol, and mixtures thereof. The alkali metal ($C_1$-$C_4$) alkoxide is preferably selected from sodium methoxide, sodium ethoxide, and mixtures thereof. It is often convenient to use about a 2 fold to about a 3 fold excess of alkali metal ($C_1$-$C_4$) alkoxide compared to 3-hydrazinopyridine·dihydrochloride. Furthermore, it is most preferred if sodium ethoxide and ethanol is used.

In another embodiment, 3-hydrazinopyridine·dihydrochloride is cyclized with methyl methacrylate in the presence of sodium ethoxide and ethanol and this mixture is heated at about 50° C. The crude 4-methyl-1-(pyridin-3-yl)pyrazolidin-3-one (1) is used as is without further purification or isolation.

In step 1b, 4-methyl-1-(pyridin-3-yl)pyrazolidin-3-one (1) is chlorinated with a chlorinating reagent in an organic solvent at a temperature from about 25° C. to about 100° C. to provide 3-(3-chloro-4-methyl-4,5-dihydro-1H-pyrazol-1-yl)pyridine (2). Suitable chlorinating reagents include phosphoryl chloride (phosphorous oxychloride), phosphorus pentachloride, and mixtures thereof. Phosphoryl chloride is currently preferred. It is often convenient to use about a 1.1 fold to about a 10 fold excess of the chlorinating reagent compared to 4-methyl-1-(pyridin-3-yl)pyrazolidin-3-one (1). The chlorination is performed in an organic solvent that does not substantially react with the chlorinating reagent. Suitable solvents include nitriles such as acetonitrile. It is currently preferred to use phosphoryl chloride as the chlorinating reagent and acetonitrile as the solvent.

In another embodiment, 4-methyl-1-(pyridin-3-yl)pyrazolidin-3-one (1) in acetonitrile is chlorinated with phosphoryl chloride and the mixture is heated to about 75° C. The 3-(3-chloro-4-methyl-4,5-dihydro-1H-pyrazol-1-yl)pyridine (2) can be isolated and purified by standard techniques.

In step 1c, 3-(3-chloro-4-methyl-4,5-dihydro-1H-pyrazol-1-yl)pyridine (2) is oxidized with an oxidant in an organic solvent at a temperature of about 25° C. to about 100° C. to provide 3-(3-chloro-4-methyl-1H-pyrazol-1-yl)pyridine (3). Suitable oxidants include copper (I) chloride in the presence of oxygen, potassium ferricyanide, and manganese (IV) oxide. It is often convenient to use about a 1.5 fold to about a 15 fold excess of oxidant compared to 3-(3-chloro-4-methyl-4,5-dihydro-1H-pyrazol-1-yl)pyridine (2). The oxidation is performed in a solvent that does not substantially react with the oxidant. Suitable solvents include water, N,N-dimethylformamide, N-methylpyrrolidinone, dichloromethane, tert-butanol, nitriles such as acetonitrile, aromatic hydrocarbons such as toluene, and mixtures thereof. It is currently preferred to use copper (I) chloride in the presence of oxygen as the oxidant, with N,N-dimethylformamide, N-methylpyrolidinone, and mixtures thereof as the solvent. It is also preferred to use potassium-ferricyanide as the oxidant, with water as the solvent. It is also preferred to use manganese (IV) oxide as the oxidant, with dichloromethane, tert-butanol, acetonitrile, toluene, and mixtures thereof as the solvent. It is also preferred to use manganese (IV) oxide as the oxidant, with acetonitrile as the solvent.

In another embodiment, 3-(3-chloro-4-methyl-4,5-dihydro-1H-pyrazol-1-yl)pyridine (2) in acetonitrile is oxidized with manganese (IV) oxide and the mixture is heated at about 40° C. The 3-(3-chloro-4-methyl-1H-pyrazol-1-yl)pyridine (3) can be isolated and purified by standard techniques.

In step 1d 3-(3-chloro-4-methyl-1H-pyrazol-1-yl)pyridine (3) is further oxidized with an oxidant in a protic solvent at a temperature of about 50° C. to about 100° C. to provide 3-chloro-1-(pyridin-3-yl)-1H-pyrazole-4-carboxylic acid (4). Suitable oxidants include potassium permanganate and sodium permanganate. It is often convenient to use about a 2.5 fold to about a 4.5 fold, preferably about a 3.0 fold excess of oxidant compared to 3-(3-chloro-4-methyl-1H-pyrazol-1-yl)pyridine (3). The oxidation is performed in a protic solvent that does not substantially react with the oxidant. Suitable solvents include water, tert-butanol, tert-amyl alcohol, and mixtures thereof.

In another embodiment, 3-(3-chloro-4-methyl-1H-pyrazol-1-yl)pyridine (3) is further oxidized by sodium permanganate in water and tert-butanol and heated at about 80° C. The 3-chloro-1-(pyridin-3-yl)-1H-pyrazole-4-carboxylic acid (4) can be isolated and purified by standard techniques.

In step 1e, 3-chloro-1-(pyridin-3-yl)-1H-pyrazole-4-carboxylic acid (4) is decarboxylated in the presence of copper oxide which may optionally be ligated with a bidentate ligand such as tetramethyl ethylenediamine in a polar aprotic solvent at a temperature from about 80° C. to about 180° C. to provide 3-(3-chloro-1H-pyrazol-1-yl)pyridine (5b). Suitable copper oxide sources include copper (I) oxide and copper (II) oxide as well as mixtures thereof. It is convenient to use about 5 wt % to about 20 wt % of copper oxide based on 3-chloro-1-(pyridin-3-yl)-1H-pyrazole-4-carboxylic acid (4). Suitable solvents include N,N-dimethylformamide, N,N-dimethylacetamide, N-methylpyrrolidinone, and mixtures thereof.

In another embodiment, 3-chloro-1-(pyridin-3-yl)-1H-pyrazole-4-carboxylic acid (4) and copper (I) oxide are mixed with N,N-dimethylacetamide and heated to about 125° C. The 3-(3-chloro-1H-pyrazol-1-yl)pyridine (5b) can be isolated and purified by standard techniques.

An illustrative example of how 3-(3-chloro-1H-pyrazol-1-yl)pyridine (5b) may be used for preparing certain pesticidal (3-halo-1-(pyridin-3-yl)-1H-pyrazol-4-yl)amides is outlined in Scheme 2.

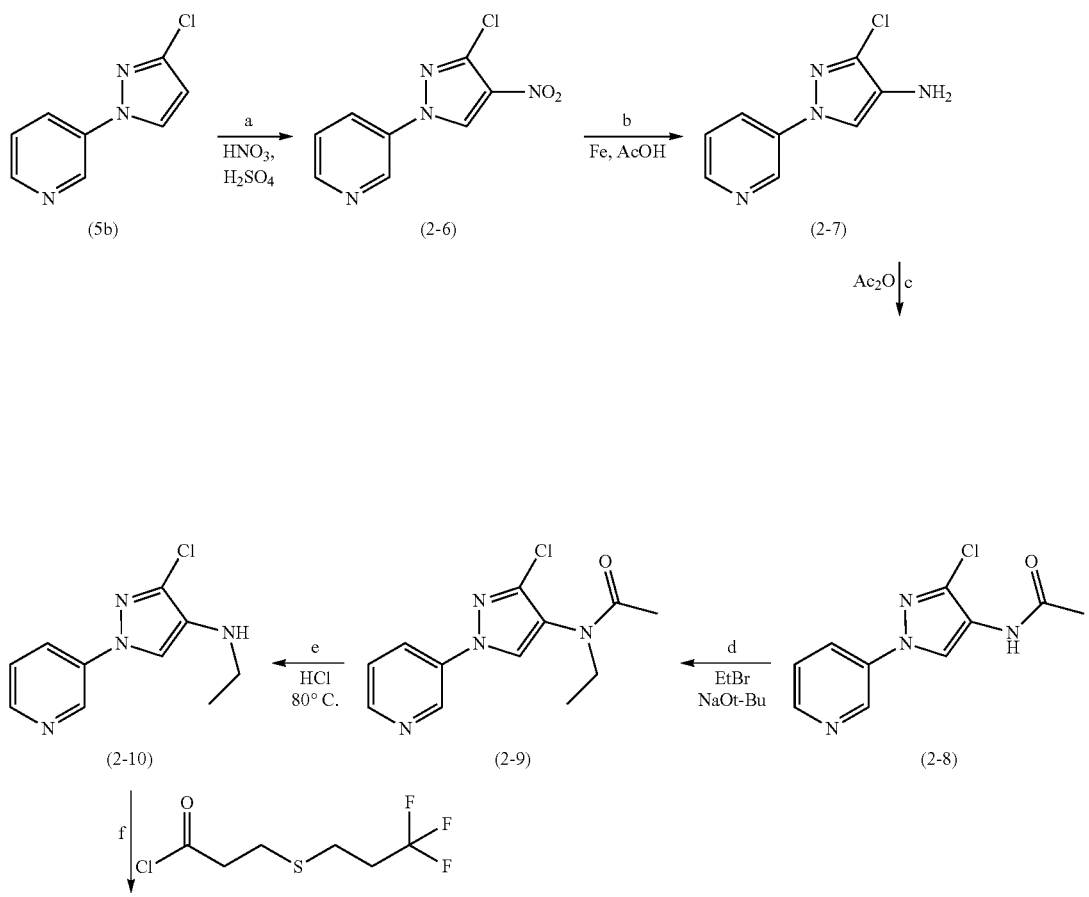

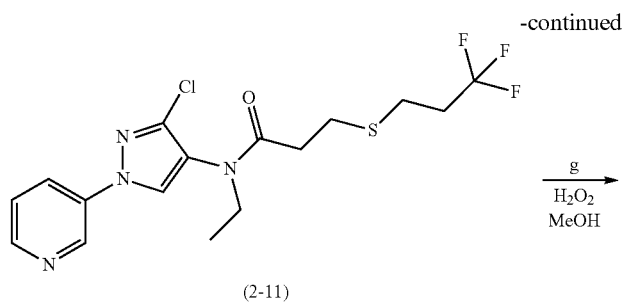

(2-11)

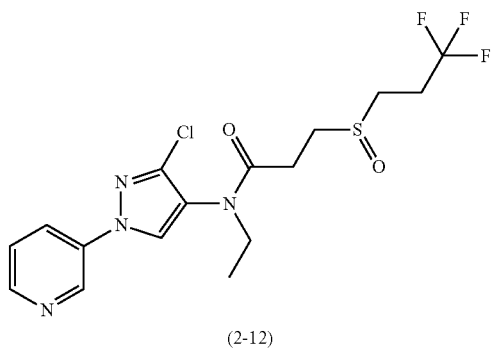

(2-12)

In step 2a, 3-(3-chloro-1H-pyrazol-1-yl)pyridine (5b) is nitrated with nitric acid (HNO₃), preferably in the presence of sulfuric acid (H₂SO₄) to yield 3-(3-chloro-4-nitro-1H-pyrazol-1-yl)pyridine (2-6). The nitration may be conducted at temperatures from about −10° C. to about 30° C.

In step 2b, 3-(3-chloro-4-nitro-1H-pyrazol-1-yl)pyridine (2-6) is reduced to yield 3-chloro-1-(pyridin-3-yl)-1H-pyrazol-4- amine (2-7). For example, 3-(3-chloro-4-nitro-1H-pyrazol-1-yl)pyridine (2-6) may be reduced with iron in acetic acid (AcOH). 3-(3-Chloro-4-nitro-1H-pyrazol-1-yl)pyridine (2-6) may also be reduced with iron and ammonium chloride (NH₄Cl). Alternatively, this reduction may be carried out using other techniques in the art, for example, 3-(3-chloro-4-nitro-1H-pyrazol-1-yl)pyridine (2-6) may be reduced using palladium on carbon in the presence of hydrogen (H₂). This reaction may be conducted at temperatures from about −10° C. to about 30° C.

In step 2c, 3-chloro-1-(pyridin-3-yl)-1H-pyrazol-4-amine (2-7) is acylated with acetylating agents such as acetyl chloride or acetic anhydride, preferably acetic anhydride (Ac₂O) to yield N-(3-chloro-1-(pyridin-3-yl)-1H-pyrazol-4-yl)acetamide (2-8). The acylation is conducted in the presence of a base, preferably an inorganic base, such as, sodium bicarbonate (NaHCO₃), and preferably, a polar solvent, such as ethyl acetate and/or tetrahydrofuran. This reaction may be conducted at temperatures from about −10° C. to about 30° C.

In step 2d, N-(3-chloro-1-(pyridin-3-yl)-1H-pyrazol-4-yl) acetamide (2-8) is alkylated with ethyl bromide (EtBr) in the presence of a base, such as sodium hydride (NaH) or sodium tert-butoxide (NaOt-Bu), in a polar aprotic solvent, such as tetrahydrofuran, at temperatures from about 20° C. to about 40° C., over a period of time of about 60 hours to about 168 hours, to yield N-(3-chloro-1-(pyridin-3-yl)-1H-pyrazol-4-yl)-N-ethylacetamide (2-9). It has been discovered that use of an iodide additive, such as potassium iodide (KI) or tetrabutylammonium iodide (TBAI) can decrease the time necessary for the reaction to occur to about 24 hours. It has also been discovered that heating the reaction at about 50° C. to about 70° C. in a sealed reactor (to prevent loss of ethyl bromide) also decreases the reaction time to about 24 hours.

In step 2e, N-(3-chloro-1-(pyridin-3-yl)-1H-pyrazol-4-ye-N-ethylacetamide (2-9) is treated with hydrochloric acid in water at temperatures from about 50° C. to about 90° C., to yield 3-chloro-N-ethyl-1-(pyridin-3-yl)-1H-pyrazol-amine (2-10). Steps d and e of Scheme 2 may also be performed without the isolation of N-(3-chloro-1-(pyridin-3-yl)-1H-pyrazol-4-yl-N-ethylacetamide (2-8).

In step 2f, 3-chloro-N-ethyl-1-(pyridin-3-yl)-1H-pyrazol-amine (2-10) is acylated with 3-((3,3,3-trifluoropropyl)thio) propanoyl chloride in the presence of a base preferably, sodium bicarbonate to yield pesticidal (3-halo-1-(pyridin-3-yl)-1H-pyrazol-4-yl)amide (2-11). The reaction may also be conducted in the absence of a base to yield pesticidal (3-halo-1-(pyridin-3-yl)-1H-pyrazol-4-yl)amide (2-11).

In step 2g, pesticidal (3-halo-1-(pyridin-3-yl)-1H-pyrazol-4-yl)amide (2-11) is oxidized with hydrogen peroxide (H₂O₂) in methanol to yield pesticidal (3-halo-1-(pyridin-3-yl)-1H-pyrazol-4-yl)amide (2-12).

EXAMPLES

These examples are for illustration purposes and are not to be construed as limiting the disclosure to only the embodiments disclosed in these examples.

Starting materials, reagents, and solvents that were obtained from commercial sources were used without further purification. Anhydrous solvents were purchased as Sure/Seal™ from Aldrich and were used as received. Melting points were obtained on a Thomas Hoover Unimelt capillary melting point apparatus or an OptiMelt Automated Melting Point System from Stanford Research Systems and are uncorrected. Examples using "room temperature" were conducted in climate controlled laboratories with temperatures ranging from about 20° C. to about 24° C. Molecules are given their known names, named according to naming programs within ISIS Draw, ChemDraw or ACD Name Pro. If such programs are unable to name a molecule, the molecule is named using conventional naming rules. ¹H NMR spectral data are in ppm (δ) and were recorded at 300, 400 or 600 MHz; ¹³C NMR spectral data are in ppm (δ) and were recorded at 75, 100 or 150 MHz, and ¹⁹F NMR spectral data are in ppm (δ) and were recorded at 376 MHz, unless otherwise stated.

1. Preparation of 4-methyl-1-(pyridin-3-yl)pyrazolidin-3-one (1)

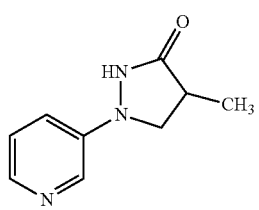

To a 250 mL three-neck round bottom flask equipped with a reflux condenser was introduced 3-hydrazinopyridine·dihydrochloride (15.0 g, 82.4 mmol). Sodium ethoxide (21 wt % in ethanol, 92.3 mL, 247 mmol) was added over 5 minutes and the pot temperature increased from 23° C. to 38° C. The resultant light brown-slurry was stirred for 10 minutes. Methyl methacrylate (17.7 mL, 165 mmol) was added slowly over 15 minutes and the pot temperature remained at 38° C. The yellow mixture was stirred at 50° C. under nitrogen for 4 hours. The mixture was then cooled down to 10° C. and hydrochloric acid (4 M in 1,4-dioxane, 20.6 mL) was added slowly to quench excess base leading to a light brown suspension. The mixture was concentrated under reduced pressure to afford the title compound as a brown solid as a mixture with sodium chloride (35.2 g, 241%): EIMS m/z 177 ([M]$^+$). The crude material was used directly in the next step.

2. Preparation of 3-(3-chloro-4-methyl-4,5-dihydro-1H-pyrazol-1-yl)pyridine (2)

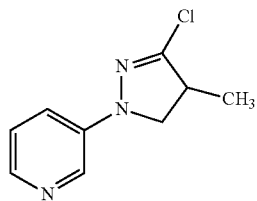

Crude 4-methyl-1-(pyridin-3-yl)pyrazolidin-3-one (35.2 g, ~82.4 mmol) was introduced into a 250 mL three-neck round bottom flask equipped with a reflux condenser. Acetonitrile (100 mL) was then added. To this yellow mixture was added phosphoryl chloride (11.56 mL, 124 mmol) slowly. The yellow slurry was stirred at 75° C. for 1 hour. The mixture was cooled down and concentrated to remove volatiles. The brown residue was carefully quenched with water (120 mL), and basified with NaOH (50 wt % in water) to pH 10 while keeping the temperature below 60° C. The mixture was then extracted with ethyl acetate (3×150 mL). The combined organic extracts were washed with water (80 mL) and concentrated under reduced pressure to afford the crude product as dark purple oil. The crude product was purified by flash column chromatography using 0-70% ethyl acetate/hexanes as eluent to provide the title compound as a brown oil (12.3 g, 76% over two steps): $^1$H NMR (400 MHz, CDCl$_3$) δ 8.27 (dd, J=2.8, 0.7 Hz, 1H), 8.15 (dd, J=4.6, 1.4 Hz, 1H), 7.38 (ddd, J=8.4, 2.9, 1.4 Hz, 1H), 7.18 (ddd, J=8.4, 4.7, 0.7 Hz, 1H), 4.17-4.06 (m, 1H), 3.47 (t, J=8.9 Hz, 1H), 3.44-3.34 (m, 1H), 1.37 (d, J=6.8 Hz, 3H); $^{13}$C NMR (101 MHz, CDCl$_3$) δ 148.17, 142.07, 141.10, 134.74, 123.39, 119.92, 56.62, 43.62, 16.16; EIMS m/z 195 ([M]$^+$).

3. Preparation of 3-(3-chloro-4-methyl-1H-pyrazol-1-yl)pyridine (3)

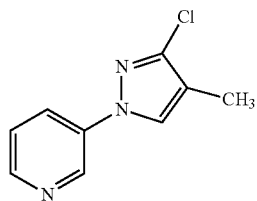

To a solution of 3-(3-chloro-4-methyl-4,5-dihydro-1H-pyrazol-1-yl)pyridine (1.0 g, 5.0 mol) in acetonitrile (10.0 mL) at 0° C. was added manganese(IV) oxide (1.3 g, 15 mmol) portionwise over 10 minutes. The mixture was slowly warmed to 22° C. over 40 minutes and then heated to 40° C. overnight. After 20 hours, additional manganese (IV) oxide (0.44 g, 5.0 mmol) was added in one portion and the mixture was stirred for 1 hour. The mixture was cooled down and filtered. The filter cake was washed with acetonitrile (3×15 mL). The organic filtrate was dried and concentrated to afford the title compound as a light yellow solid (0.92 g, 95%): $^1$H NMR (400 MHz, CDCl$_3$) δ 8.90 (dd, J=2.6, 0.8 Hz, 1H), 8.52 (dd, J=4.8, 1.5 Hz, 1H), 7.99 (ddd, J=8.3, 2.7, 1.4 Hz, 1H), 7.74 (q, J=0.9 Hz, 1H), 7.39 (ddd, J=8.3, 4.8, 0.8 Hz, 1H), 2.13 (d, J=0.9 Hz, 3H); $^{13}$C NMR (101 MHz, CDCl$_3$) δ 147.26, 142.87, 139.53, 135.90, 126.53, 125.69, 123.84, 116.86, 22.47; EIMS m/z 193 ([M]$^+$).

4. Preparation of 3-chloro-1-(pyridin-3-yl)-1H-pyrazole-4-carboxylic acid (4)

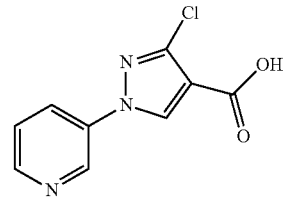 [SMILES: O=C(O)c1cn(-c2cccnc2)nc1Cl]

To a mixture of 3-(3-chloro-4-methyl-4,5-dihydro-1H-pyrazol-1-yl)pyridine (2.0 g, 10 mmol) in water (10.0 mL) and tert-butanol (5.0 mL) was added a solution of sodium permanganate (NaMnO4) (5.0 g, 35 mmol) in water (15 mL) over 20 minutes. The mixture was heated to 80° C. and stirred overnight. Additional sodium permanganate (0.711 g, 5.0 mmol) in water (2.0 mL) was added after 16 hours and the mixture was stirred for another 4 hours. The dark mixture was filtered through Celite®, washed with water (5.0 mL) and ethyl acetate (3×15 mL). The aqueous layer was extracted with ethyl acetate (25 mL) and acidified with concentrated hydrochloric acid to pH 5 leading to white precipitate which was collected by filtration. The filtrate was concentrated leading to white precipitate which was collected by filtration and washed with water (2.0 mL). The solid products were combined and dried under high vacuum to afford the title compound as a white solid (1.0 g, 46%): $^1$H NMR (400 MHz, DMSO-d$_6$) δ 9.11 (s, 2H), 8.59 (d, J=4.7, 1H), 8.28 (ddd, J=8.4, 2.7, 1.4 Hz, 1H), 7.58 (dd, J=8.0, 4.4 Hz, 1H); $^{13}$C NMR (101 MHz, DMSO-d$_6$) δ 162.24, 148.35, 141.46, 140.21, 135.01, 134.01, 126.45, 124.23, 115.34; ESIMS m/z 224 ([M+H]$^+$).

5. Preparation of 3-(3-chloro-1H-pyrazol-1-yl)pyridine (5b)

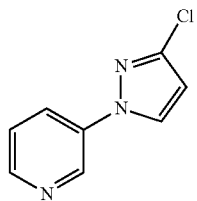 [SMILES: Clc1ccn(-c2cccnc2)n1]

To a mixture of 3-chloro-1-(pyridin-3-yl)-1H-pyrazole-4-carboxylic acid (0.223 g, 1.0 mmol) in N,N-dimethylacetamide (3.0 mL) was added copper (I) oxide (0.022 g, 10 wt %). The mixture was heated to 125° C. and stirred for 6 hours. The brown mixture was filtered and washed with N,N-dimethylacetamide (1.0 mL) and acetonitrile (2×2 mL). The light yellow filtrate was analyzed by LC using di-n-propyl phthalate as internal standard (0.124 g, 69% in-pot yield); mp 66-68° C.; $^1$H NMR (400 MHz, CDCl$_3$) δ 8.93 (d, J=27 Hz, 1H), 8.57 (dd, J=4.8, 1.4 Hz, 1H), 8.02 (ddd, J=8.3, 2.7, 1.5 Hz, 1H), 7.91 (d, J=2.6 Hz, 1H), 7.47-7.34 (m, 1H), 6.45 (d, J=2.6 Hz, 1H); $^{13}$C NMR (101 MHz, CDCl$_3$) δ 148.01, 142.72, 140.12, 135.99, 128.64, 126.41, 124.01, 108.0; ESIMS m/z 180 ([M+]$^+$).

6. Preparation of 3-(3-chloro-4-nitro-1H-pyrazol-1-yl)pyridine (2-6)

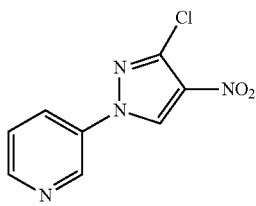 [SMILES: O=[N+]([O-])c1cn(-c2cccnc2)nc1Cl]

To a 100 mL, round bottom flask was charged 3-(3-chloro-1H-pyrazol-1-yl)pyridine (2.00 g, 11.1 mmol) and concentrated sulfuric acid (4 mL). This suspension was cooled to 5° C. and 2:1 concentrated nitric acid/sulfuric acid (3 mL, prepared by adding the concentrated sulfuric acid to a stirring and cooling solution of the nitric acid) was added dropwise at a rate such that the internal temperature was maintained <15° C. The reaction was allowed to warm to 20° C. and stirred for 18 hours. A sample of the reaction mixture was carefully diluted into water, basified with sodium hydroxide (50 wt % in water) and extracted with ethyl acetate. Analysis of the organic layer indicated that the reaction was essentially complete. The reaction mixture was carefully added to ice cold water (100 mL) at <20° C. It was basified with sodium hydroxide (50 wt % in water) at <20° C. The resulting light yellow suspension was stirred for 2 hours and filtered. The filter cake was rinsed with water (3×20 mL) and dried to afford an off-white solid (2.5 g, quantitative): mp 141-143° C.; $^1$H NMR (400 MHz, DMSO-d$_6$) δ 9.86 (s, 1H), 9.23-9.06 (m, 1H), 8.75-8.60 (m, 1H), 8.33 (ddd, J=8.4, 2.8, 1.4 Hz, 1H), 7.64 (ddd, J=8.5, 4.7, 0.7 Hz, 1H); $^{13}$C NMR (101 MHz, DMSO-d$_6$) δ 149.49, 140.75, 136.02, 134.43, 132.14, 131.76, 127.22, 124.31; EIMS m/z 224 ([M]$^+$).

7. Preparation of 3-(3-chloro-4-amino-1H-pyrazol-1-yl)pyridine (2-7)

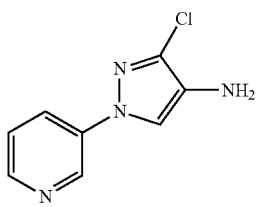 [SMILES: Nc1cn(-c2cccnc2)nc1Cl]

To a 100 mL, 3-neck round bottom flask was charged 3-(3-chloro-4-nitro-1H-pyrazol-1-yl)pyridine (2.40 g, 10.7 mmol), acetic acid (4 mL), ethanol (4.8 mL) and water (4.8 mL). The mixture was cooled to 5° C. and iron powder (2.98 g, 53.4 mmol) was added portionwise over ~15 minutes. The reaction was allowed to stir at 20° C. for 18 hours and diluted to 50 mL with water. It was filtered through Celite® and the filtrate was carefully basified with a sodium hydroxide solution (50 wt % in water). The resulting suspension was filtered through Celite® and the filtrate was extracted with ethyl acetate (3×20 mL). The organic layers were combined, dried over sodium sulfate and concentrated to dryness to afford a tan colored solid, which was further dried under vacuum for 18 hours (2.20 g, quantitative): mp 145-147° C.; $^1$H NMR (400 MHz, DMSO-d$_6$) δ 8.95 (dd, J=2.6, 0.8 Hz, 1H), 8.45 (dd, J=4.7, 1.4 Hz, 1H), 8.08 (ddd, J=8.4, 2.7, 1.4 Hz, 1H), 7.91 (s, 1H), 7.49 (ddd, J=8.3, 4.7, 0.8 Hz, 1H), 4.43 (s, 2H); $^{13}$C NMR (101 MHz, DMSO-d$_6$) δ 146.35, 138.53, 135.72, 132.09, 130.09, 124.29, 124.11, 114.09; EIMS m/z 194 ([M]$^+$).

Alternate synthetic route to 3-(3-chloro-4-amino-1H-pyrazol-1-yl)pyridine (2-7): In a 250 mL 3-neck round bottom flask was added 3-(3-chloro-4-nitro-1H-pyrazol-1-yl)pyridine (5.00 g, 21.8 mmol), ethanol (80 mL), water (40 mL), and ammonium chloride (5.84 g, 109 mmol). The suspension was stirred under nitrogen stream for 5 minutes then iron powder (4.87 g, 87.2 mmol) was added. The reaction mixture was heated to reflux (~80° C.) and held there for 4 hours. After 4 hours a reaction aliquot taken and the reaction had gone to full conversion as shown by HPLC analysis. Ethyl acetate (120 mL) and Celite® (10 g) were added to the reaction mixture and the mixture was let stir for 10 minutes. The black colored suspension was then filtered via a Celite® pad and rinsed with ethyl acetate (80 mL) The filtrate was washed with saturated sodium bicarbonate solution in water (30 mL) and the organic layer was assayed. The assay gave 4.19 g (99% yield) of product. The organic solvent was removed in vacuo to give a brown colored crude solid that was used without further purification.

8. N-(3-Chloro-1-(pyridin-3-yl)-1H-pyrazol-4-yl)acetamide (2-8)

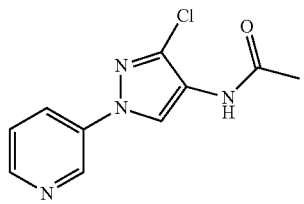 [SMILES: CC(=O)Nc1cn(-c2cccnc2)nc1Cl]

A 100 mL three-neck round bottom flask was charged with 3-chloro-1(pyridin-3-yl)-1H-pyrazol-4-amine (1.00 g, 5.14 mmol) and ethyl acetate (10 mL). Sodium bicarbonate (1.08 g, 12.9 mmol) was added, followed by dropwise addition of acetic anhydride (0.629 g, 6.17 mmol) at <20° C. The reaction was stirred at 20° C. for 2 hours to afford a suspension, at which point thin layer chromatography analysis [Eluent: ethyl acetate] indicated that the reaction was complete. The reaction was diluted with water (50 mL) and the resulting suspension was filtered. The solid was rinsed with water (10 mL) followed by methanol (5 mL). The solid was further dried under vacuum at 20° C. to afford the desired product as a white solid (0.804 g, 66%): mp 169-

172° C.; $^1$H NMR (400 MHz, DMSO-d$_6$) δ 9.84 (s, 1H), 9.05 (dd, J=2.8, 0.8 Hz, 1H), 8.82 (s, 1H), 8.54 (dd, J=4.7, 1.4 Hz, 1H), 8.20 (ddd, J=8.4, 2.8, 1.4 Hz, 1H), 7.54, (ddd, J=8.3, 4.7, 0.8 Hz, 1H), 2.11 (s, 3H); $^{13}$C NMR (101 MHz, DMSO-d$_6$) δ 168.12, 147.46, 139.42, 135.46, 133.60, 125.47, 124.21, 122.21, 120,16, 22.62; EIMS m/z 236 ([M]$^+$).

9. Preparation of N-(3-chloro-1-(pyridin-3-yl)-1H-pyrazol-4-yl)-N-ethylacetamide (2-9)

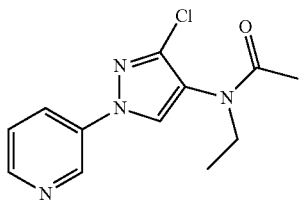 [SMILES: CCN(C(C)=O)c1cn(-c2cccnc2)nc1Cl]

In 125 mL 3-neck round-bottomed flask was added N-(3-chloro-1-(pyridin-3-yl)-1H-pyrazol-4-yl)acetamide (2.57 g, 9.44 mmol), tetrahydrofuran (55 mL), and sodium tert-butoxide (1.81 g, 18.9 mmol). The suspension was stirred for 5 minutes then ethyl bromide (1.41 mL, 18.9 mmol), and tetrabutylammonium iodide (67 mg, 0.2 mmol) were added. The resulting gray colored suspension was then heated to 38° C. The reaction was analyzed after 3 hours and found to have gone to 81% completion, after 24 hours the reaction was found to have gone to completion. The reaction mixture was allowed to cool to ambient temperature and quenched with ammonium hydroxide/formic acid (HCO$_2$H) buffer (10 mL). The mixture was then diluted with tetrahydrofuran (40 mL), ethyl acetate (120 mL), and saturated sodium bicarbonate solution in water (30 mL). The layers were separated and the aqueous layer was extracted with ethyl acetate (2×30 mL). The organic layers were combined and silica gel (37 g) was added. The solvent was removed in vacuo to give a solid that was purified using semi-automated silica gel chromatography (RediSep Silica 220 g column; Hexanes (0.2% triethylamine)/ethyl acetate, 40/60 to 0/100 gradient elution system, flow rate 150 mL/minute) to give, after concentration, an orange solid (2.19 g, 88%).

10. Preparation of 3-chloro-N-ethyl-1-(pyridin-3-yl)-1H-pyrazol-4-amine (2-10)

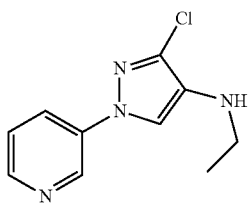

A solution of N-(3-chloro-1-(pyridin-3-yl)-1H-pyrazol-4-yl)-N-ethylacetamide (1.8 g, 6.80 mmol) in 1 N hydrochloric acid (34 mL) was heated at 80° C. for 18 hours, at which point HPLC analysis indicated that only 1.1% starting material remained. The reaction mixture was cooled to 20° C. and basified with sodium hydroxide (50 wt % in water) to pH>9. The resulting suspension was stirred at 20° C. for 2 hours and filtered. The filter cake was rinsed with water (2×5 mL), conditioned for 30 minutes, and air-dried to afford an off-white solid (1.48 g, 95%): $^1$H NMR (400 MHz, DMSO-d$_6$) δ 9.00 (dd, J=2.8, 0.8 Hz, 1H), 8.45 (dd, J=4.7, 1.4 Hz, 1H), 8.11 (ddd, J=8.4, 2.8, 1.4 Hz, 1H), 8.06 (d, J=0.6 Hz, 1H), 7.49 (ddd, J=8.4, 4.7, 0.8 Hz, 1H), 4.63 (t, J=6.0 Hz, 1H), 3.00 (qd, J=7.1, 5.8 Hz, 2H), 1.19 (t, J=7.1 Hz, 3H); $^{13}$C NMR (101 MHz, DMSO-d$_6$) δ 146.18, 138.31, 135.78, 132.82, 130.84, 124.08, 123.97, 112.23, 40.51, 14.28; ESIMS m/z 223 ([M+H]$^+$).

Alternate synthetic route to 3-chloro-N-ethyl-1-(pyridin-3-yl)-1H-pyrazol-amine (2-10):

To a 3-neck, 100-mL round bottom flask was charged N-(3-chloro-1-(pyridin-3-yl)-1H-pyrazol-4-yl)acetamide (5 g, 21.13 mmol) and tetrahydrofuran (50 mL). Sodium tert-butoxide (4.06 g, 42.3 mmol) was added (causing a temperature rise from 22° C. to 27.6° C.), followed by ethyl bromide (6.26 mL, 85 mmol). The reaction was stirred at 35° C. for 144 h at which point only 3.2% (AUC) starting material remained. The reaction mixture was concentrated to give a brown residue, which was dissolved in 1 N hydrochloric acid (106 mL, 106 mmol) and heated at 80° C. for 24 hours, at which point HPLC analysis indicated that the starting material had been consumed. The reaction was cooled to 20° C. and basified with sodium hydroxide (50 wt % in water) to pH>9. The resulting suspension was stirred at 20° C. for 1 hour and filtered. The filter cake was rinsed with water (25 mL) to afford a brown solid (5.18 g). The resulting crude product was dissolved in ethyl acetate and passed through a silica gel plug (50 g) using ethyl acetate (500 mL) as eluent. The filtrate was concentrated to dryness to afford a white solid (3.8 g, 80%).

11. Preparation of N-(3-chloro-1-(pyridin-3-yl)-1H-pyrazol-4-yl)-N-ethyl-3-((3,3,3-trifluoropropyl)thio)propanamide (2-11)

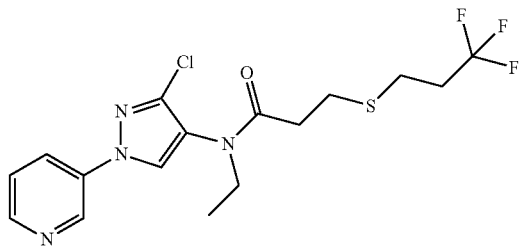 [SMILES: CCN(C(=O)CCSCCC(F)(F)F)c1cn(-c2cccnc2)nc1Cl]

A 100 mL three neck round bottom flask was charged with 3-chloro-N-ethyl-1-(pyridine-3-yl)-1H-pyrazol-4-amine (5.00 g, 22.5 mmol) and ethyl acetate (50 mL). Sodium bicarbonate (4.72 g, 56.1 mmol) was added, followed by dropwise addition of 3-((3,3,3-trifluoropropyl)thio)propanoyl chloride (5.95 g, 26.9 mmol) at <20° C. for 2 hours, at which point HPLC analysis indicated that the reaction was complete. The reaction was diluted with water (50 mL) (off-gassing) and the layers were separated. The aqueous layer was extracted with ethyl acetate (20 mL) and the combined organic layers were concentrated to dryness to afford a light brown solid (10.1 g, quantitative). A small sample of crude product was purified by flash column chromatography using ethyl acetate as eluent to obtain an analytical sample: mp 79-81° C.; $^1$H NMR (400 MHz, DMSO-d$_6$) δ 9.11 (d, J=2.7 Hz, 1H), 8.97 (s, 1H), 8.60 (dd, J=4.8, 1.4 Hz, 1H), 8.24 (ddd, J=8.4, 2.8, 1.4 Hz, 1H), 7.60

(ddd, J=8.4, 4.7, 0.8 Hz, 1H), 3.62 (q, J=7.2 Hz, 2H), 2.75 (t, J=7.0 Hz, 2H), 2.66-2.57 (m 2H), 2.57-2.44 (m, 2H), 2.41 (t, J=7.0 Hz, 2H), 1.08 (t, J=7.1 Hz, 3H). EIMS m/z 406 ([M]+).

12. Preparation of N-(3-chloro-1-(pyridin-3-yl)-1H-pyrazol-4-yl)-N-ethyl-3-((3,3,3-trifluoropropyl)sulfoxo)propanamide (2-12)

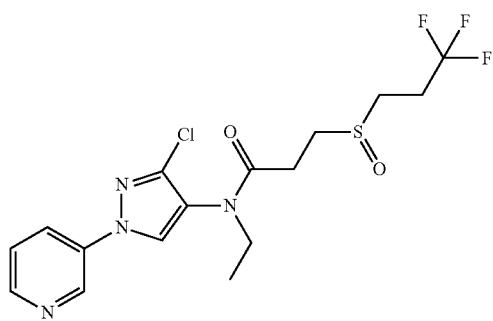 [SMILES: CCN(C(=O)CCS(=O)CCC(F)(F)F)c1cn(-c2cccnc2)nc1Cl]

N-(3-Chloro-1-(pyridin-3-yl)-1H-pyrazol-4-yl)-N-ethyl-3-((3,3,3-trifluoropropyl)thio) propanamide (57.4 g, 141 mmol) was stirred in methanol (180 mL). To the resulting solution was added hydrogen peroxide (43.2 mL, 423 mmol) dropwise using a syringe. The solution was stirred at room temperature for 6 hours, at which point LCMS analysis indicated that the starting material was consumed. The mixture was poured into dichloromethane (360 mL) and washed with aqueous sodium carbonate ($Na_2CO_3$). The organic layer was dried over sodium sulfate and concentrated under reduced pressure to provide a thick yellow oil. The crude product was purified by flash column chromatography using 0-10% methanol/ethyl acetate as eluent. The pure fractions were combined and concentrated to afford the desired product as an oil (42.6 g, 68%): $^1$H NMR (400 MHz, DMSO-$d_6$) δ 9.09 (dd, J=2.8, 0.7 Hz, 1H), 8.98 (s, 1H), 8.60 (dd, J=4.7, 1.4 Hz, 1H), 8.24 (ddd, J=8.4, 2.7, 1.4 Hz, 1H), 7.60 (ddd, J=8.4, 4.7, 0.8 Hz, 1H), 3.61 (q, J=7.4, 7.0 Hz, 2H), 3.20-2.97 (m, 2H), 2.95-2.78 (m, 2H), 2.76-2.57 (m, 2H), 2.58-2.45 (m, 2H), 1.09 (t, J=7.1 Hz, 3H); ESIMS m/z 423 ([M+H]+).

Example A Bioassays on Green Peach Aphid ("GPA") (*Myzus persicae*) (MYZUPE.)

GPA is the most significant aphid pest of peach trees, causing decreased growth, shriveling of leaves, and the death of various tissues. It is also hazardous because it acts as a vector for the transport of plant viruses, such as potato virus Y and potato leafroll virus to members of the nightshade/potato family Solanaceae, and various mosaic viruses to many other food crops. GPA attacks such plants as broccoli, burdock, cabbage, carrot, cauliflower, daikon, eggplant, green beans, lettuce, macadamia, papaya, peppers, sweet potatoes, tomatoes, watercress and zucchini among other plants. GPA also attacks many ornamental crops such as carnations, chrysanthemum, flowering white cabbage, poinsettia and roses. GPA has developed resistance to many pesticides.

Several molecules disclosed herein were tested against GPA using procedures described below.

Cabbage seedling grown in 3-in pots, with 2-3 small (3-5 cm) true leaves, were used as test substrate. The seedlings were infested with 20-5-GPA (wingless adult and nymph stages) one day prior to chemical application. Four posts with individual seedlings were used for each treatment. Test compounds (2 mg) were dissolved in 2 mL of acetone/methanol (1:1) solvent, forming stock solutions of 1000 ppm test compound. The stock solutions were diluted 5× with 0.025% Tween 20 in water to obtain the solution at 200 ppm test compound. A hand-held aspirator-type sprayer was used for spraying a solution to both sides of the cabbage leaves until runoff. Reference plants (solvent check) were sprayed with the diluent only containing 20% by volume acetone/methanol (1:1) solvent. Treated plants were held in a holding room for three days at approximately 25° C. and ambient relative humidity (RH) prior to grading. Evaluation was conducted by counting the number of live aphids per plant under a microscope. Percent Control was measured by using Abbott's correction formula (W. S. Abbott, "A Method of Computing the Effectiveness of an Insecticide" J. Econ. Entomol 18 (1925), pp. 265-267) as follows.

$$\text{Corrected \% Control} = 100 \times (X - Y)/X$$

where
X=No. of live aphids on solvent check plants and
Y=No. of live aphids on treated plants The results are indicated in the table entitled "Table 1: GPA (MYZUPE) and sweetpotato whitefly-crawler (BEMITA) Rating Table".

Example B Bioassays on Sweetpotato Whitefly Crawler (*Bemisia tabaci*) (BEMITA.)

The sweetpotato whitefly, *Bemisia tabaci* (*Gennadius*), has been recorded in the United States since the late 1800s. In 1986 in Florida, *Bemisia tabaci* became an extreme economic pest. Whiteflies usually feed on the lower surface of their host plant leaves. From the egg hatches a minute crawler stage that moves about the leaf until it inserts its microscopic, threadlike mouthparts to feed by sucking sap from the phloem. Adults and nymphs excrete honeydew (largely plant sugars from feeding on phloem), a sticky, viscous liquid in which dark sooty molds grow. Heavy infestations of adults and their progeny can cause seedling death, or reduction in vigor and yield of older plants, due simply to sap removal. The honeydew can stick cotton lint together, making it more difficult to gin and therefore reducing its value. Sooty mold grows on honeydew-covered substrates, obscuring the leaf and reducing photosynthesis, and reducing fruit quality grade. It transmitted plant-pathogenic viruses that had never affected cultivated crops and induced plant physiological disorders, such as tomato irregular ripening and squash silverleaf disorder. Whiteflies are resistant to many formerly effective pesticides.

Cotton plants grown in 3-inch pots, with 1 small (3-5 cm) true leaf, were used at test substrate. The plants were placed in a room with whitefly adults. Adults were allowed to deposit eggs for 2-3 days. After a 2-3 day egg-laying period, plants were taken from the adult whitefly room. Adults were blown off leaves using a hand-held Devilbliss sprayer (23 psi). Plants with egg infestation (100-300 eggs per plant) were placed in a holding room for 5-6 days at 82° F. and 50% RH for egg hatch and crawler stage to develop. Four cotton plants were used for each treatment. Compounds (2 mg) were dissolved in 1 mL of acetone solvent, forming stock solutions of 2000 ppm. The stock solutions were diluted 10× with 0.025% Tween 20 in water to obtain a test solution at 200 ppm. A hand-held Devilbliss sprayer was used for spraying a solution to both sides of cotton leaf until runoff. Reference plants (solvent check) were sprayed with the diluent only. Treated plants were held in a holding room for 8-9 days at approximately 82° F. and 50% RH prior to grading. Evaluation was conducted by counting the number of live nymphs per plant under a microscope. Pesticidal activity was measured by using Abbott's correction formula (see above) and presented in Table 1.

TABLE 1

GPA (MYZUPE) and sweetpotato whitefly-crawler (BEMITA) Rating Table

| Example Compound | BEMITA | MYZUPE |
|---|---|---|
| Compound 2 | C | C |
| Compound 3 | C | C |
| Compound 2-11 | A | A |
| Compound 2-12 | A | A |

| % Control of Mortality | Rating |
|---|---|
| 80-100 | A |
| More than 0-Less than 80 | B |
| Not Tested | C |
| No activity noticed in this bioassay | D |

What is claimed is:

1. A process for preparing 3-(3-chloro-1H-pyrazol-1-yl)pyridine (5b)

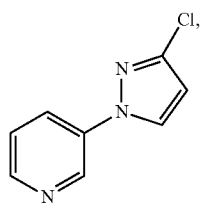

comprising contacting 3-chloro-1-(pyridin-3-yl)-1H-pyrazole-4-carboxylic acid (4)

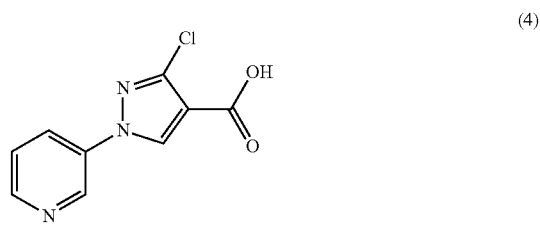 [SMILES: O=C(O)c1cn(-c2cccnc2)nc1Cl]

with copper oxide in a polar aprotic solvent at a temperature of about 80° C. to about 180° C. to provide 3-(3-chloro-1H-pyrazol-1-yl)pyridine (5b).

2. The process of claim 1, wherein the copper oxide is ligated with a bidentate ligand.

3. The process of claim 2, wherein the bidentate ligand is tetramethyl ethylenediamine.

4. The process of claim 1, wherein the copper oxide is copper(I) oxide or copper(II) oxide.

5. The process of claim 1, wherein the copper oxide is used in about 5 wt % to about 20 wt % based on 3-chloro-1-(pyridin-3-yl)-1H-pyrazole-4-carboxylic acid.

6. The process of claim 1, wherein the polar aprotic solvent is selected from the group consisting of N,N-dimethylformamide, N,N-dimethylacetamide, N-methylpyrrolidinone, and mixtures thereof.

7. The process of claim 1, wherein the copper oxide is copper(I) oxide, and the polar aprotic solvent is N,N-dimethylacetamide.

* * * * *